United States Patent [19]

Edwards

[11] 4,396,779
[45] Aug. 2, 1983

[54] ALKANOL ALKOXYLATE PREPARATION

[75] Inventor: Charles L. Edwards, Houston, Tex.

[73] Assignee: Shell Oil Company, Houston, Tex.

[21] Appl. No.: 366,438

[22] Filed: Apr. 7, 1982

[51] Int. Cl.$^3$ .............................................. C07C 41/03
[52] U.S. Cl. ..................................... 568/618; 568/121
[58] Field of Search ................................. 568/618, 621

[56] References Cited

U.S. PATENT DOCUMENTS 3,000,963  9/1961  Speranza .............................. 568/621
4,282,387  8/1981  Olstowski ............................. 568/619

*Primary Examiner*—Howard T. Mars

[57] ABSTRACT

A process for the preparation of alkanol alkoxylates, useful as nonionic surfactants, comprises steps for alkoxylating one or more alkanols having carbon number in the range from 8 to 18 by reaction with one or more alkylene oxides having carbon number in the range from 2 to 4 under alkaline pH and in the presence of one or more soluble compounds of calcium, and neutralizing the resulting alkoxylation mixture by addition thereto of an acid selected from the group consisting of propionic acid, benzoic acid, and mixtures thereof. The products are characterized by a single liquid phase of low viscosity.

5 Claims, 1 Drawing Figure

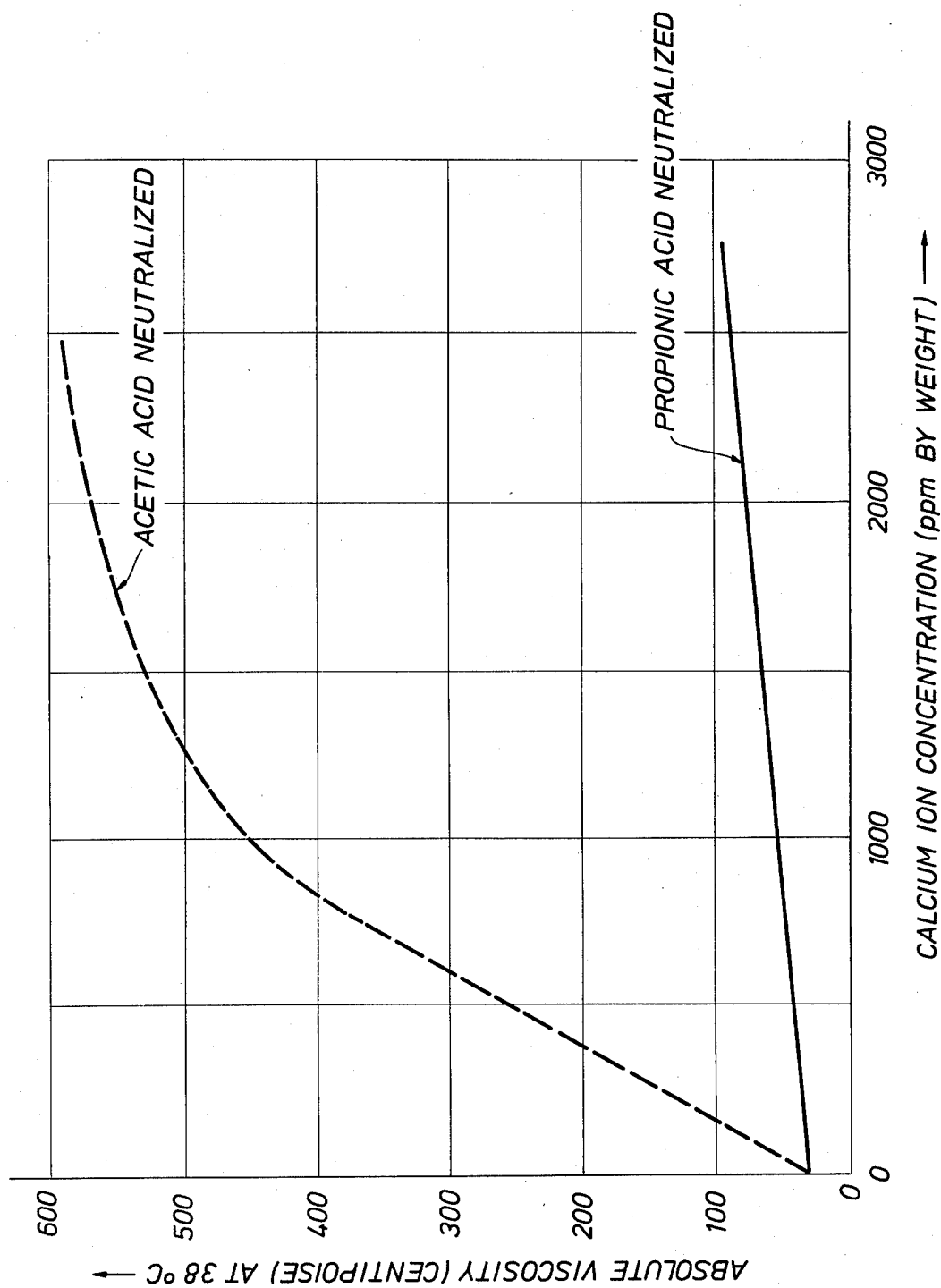

ALKANOL ALKOXYLATE PREPARATION

BACKGROUND OF THE INVENTION

This invention relates to the preparation of alkanol alkoxylates via the catalyzed addition reaction of alkylene oxides with alkanols. More specifically, this invention is directed to a process for the preparation of an alkanol alkoxylate which comprises the reaction of an alkanol with an alkylene oxide in the presence of a basic calcium-containing catalyst and the neutralization of the resulting reaction mixture with an organic acid of critical definition.

Alkanol alkoxylates (or simply alkoxylates, as the terminology is alternatively applied herein) are known materials having utility, for instance, as solvents, surfactants, and chemical intermediates. Alkoxylates in which the alkyl group has a number of carbon atoms in the detergent-range, i.e., from about 8 to 20, are common components of commercial cleaning formulations for use in industry and in the home.

Under conventional practice, alkoxylates are typically prepared by the addition reaction of alkylene oxides with alkanols. In the particular case of the preparation of an ethoxylate (represented by formula III below) the addition of number (n) of ethylene oxide molecules (formula II) to a single alkanol molecule (formula I) is illustrated by the equation

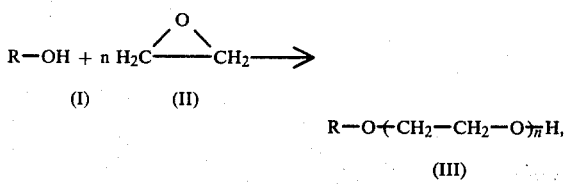

$$R-OH + n\ H_2C\overset{O}{\underset{}{\diagup\!\!\!\diagdown}} CH_2 \longrightarrow$$

(I)   (II)

$$R-O(CH_2-CH_2-O)_nH,$$

(III)

wherein R is alkyl and n is an integer equal to or greater than one. The product of such an alkoxylation reaction is a mixture of various alkoxylate molecules having a variety of alkylene oxide adducts, i.e., a mixture of compounds with different values of n.

Alkoxylation reactions between alkylene oxides and alkanols are known to be necessarily carried out in the presence of a catalyst, which may be either of acidic or, preferably, basic character. Suitable basic catalysts are recognized to include the soluble basic salts of the alkali metals of Group I of the Periodic Table, e.g., lithium, sodium, potassium, rubidium, and cesium, and the soluble basic salts of certain of the alkaline earth metals of Group II, e.g., barium and strontium.

With particular regard to calcium-containing catalysts as are employed in the process of this invention, the published European patent application Nos. 26,544, 26,546, and 26,547 describe alkoxylation reactions catalyzed by soluble basic calcium compounds. U.S. Pat. No. 4,302,613 describes the use of certain calcium compounds as co-catalysts in alkoxylation reactions.

Following an alkoxylation reaction carried out in the presence of a soluble catalyst, it is generally necessary to neutralize the reaction mixture, typically to a pH of about 5.0 to 7.0 by addition of an organic acid. Neutralization is required because a quantity of base sufficient to catalyze the alkoxylation would, if it remained unneutralized, promote chemical instability in the product. Under conventional commercial practice, acetic acid is utilized in essentially all cases for catalyst neutralization during preparation of alkoxylates.

The preparation of alkoxylates via the reaction between alkanols and alkylene oxides catalyzed by soluble, basic calcium catalysts, while not now commercially practiced, is of particular advantage for several reasons, including the characteristic narrow-range distribution of alkylene oxide adducts in the alkoxylate product molecules, the activity and selectivity of the catalysts, and the negligible toxicity of the catalysts and catalyst residues. However, it is now observed that when neutralized with acetic acid the calcium-containing alkoxylation reaction mixture is a product having physical properties unacceptable for many applications. In combination (and in the presence of the alkoxylate) even relatively small quantities of the calcium ion and the acetic acid interact to produce a semi-solid or gel-like alkoxylate product of high viscosity. The handling properties of this product are in sharp contrast to those of the liquid products of common conventional alkoxylation processes, and are of substantial disadvantage in storage, transportation, formulation, and application to detergent and other services. Accordingly, a process for the preparation of a neutralized alkanol alkoxylate product of low viscosity, from $C_8$ to $C_{18}$ alkanols and $C_2$ to $C_4$ alkylene oxide via a calcium-catalyzed alkoxylation reaction, would be most desirable.

SUMMARY OF THE INVENTION

It has now been found that alkoxylation reactions carried out in the presence of soluble basic calcium compounds can be utilized to prepare alkoxylate products which remain fluid after neutralization of the resulting reaction mixture if the organic acid utilized for neutralization purposes is selected from the group consisting of propionic acid and benzoic acid. The use of either propionic acid or benzoic acid is found to be critical to the invention. Other organic acids which would be acceptable, e.g., from the standpoint of toxicity, odor, etc., and particularly other carboxylic acids yield neutralized alkoxylate products which suffer from one or more disadvantages such as gel or precipitate formation.

Accordingly, the present invention is briefly described as a process for the preparation of alkanol alkoxylates which comprises steps for alkoxylating one or more $C_8$ to $C_{18}$ alkanols by reaction with one or more $C_2$ to $C_4$ alkylene oxides under alkaline pH in the presence of one or more soluble calcium compounds, and neutralizing the resulting alkoxylation mixture by addition thereto of an acid selected from the group consisting of propionic acid, benzoic acid, and mixtures thereof.

BRIEF DESCRIPTION OF THE DRAWING

The attached drawing provides comparative illustration of the viscosities of calcium-containing ethoxylation products in one case neutralized with propionic acid in accordance with the invention and in another case neutralized with acetic acid, not in accordance with the invention.

DESCRIPTION OF THE PREFERRED EMBODIMENTS

A necessary step in the process of the invention is the preparation of an alkanol alkoxylate by reaction of $C_8$ to $C_{18}$ alkanol with $C_2$ to $C_4$ alkylene oxide under basic conditions and in the presence of dissolved calcium.

Apart from aspects relating to the presence of calcium in the reaction mixture, this step of the process of the invention is suitably conducted under processing procedures and reaction conditions well known to the art for base-catalyzed alkoxylation reactions.

Still, for purposes of the invention, particular preferences may be stated for certain processing parameters. For instance, the alkoxylation reaction is preferably carried out at a temperature in the range from about 90° to 250° C. A more preferred range is that from about 130° to 210° C., while a temperature between about 145° and 190° C. is still more preferred. Considered most preferred is a reaction temperature in the range from about 155° to 175° C. Although the pressure under which the alkoxylation reaction is conducted is not critical to the invention, a total pressure in the range from about 0 to 150 psig is preferred. Under preferred conditions of temperature and pressure, the alkanol reactant is generally liquid and the alkylene oxide reactant a vapor. The reaction is then most conveniently conducted by contacting gaseous alkylene oxide with a liquid solution of the alkoxylation catalyst in the alkanol. Since, as is known, there is a danger of explosion in alkylene oxides maintained in concentrated form at elevated temperature and pressure, the partial pressure of the alkylene oxide in the vapor phase is preferably limited, for instance, to less than about 60 psia, and this reactant is diluted with an inert gas such as nitrogen, for instance, to a vapor phase concentration of about 50 percent or less. The reaction can, however, be safely accomplished at greater alkylene oxide concentration, greater total pressure and greater partial pressure of alkylene oxide if suitable precautions, known to the art, are taken to manage the risks of explosion. A total pressure of between about 40 and 110 psig, with an alkylene oxide partial pressure between about 15 and 60 psia, is particularly preferred, while a total pressure of between about 50 and 90 psig, with an alkylene oxide partial pressure between about 20 and 50 psia is considered more preferred.

The alkanol reactant that is suitable for use in practice of the present invention comprises, in the broad sense, one or more of the same $C_8$ and $C_{18}$ alkanols as have been heretofore recognized as suitable for alkoxylation by reaction with alkylene oxides in the presence of basic catalysts, for example, those alkanols described as suitable for this purpose in the above-referenced U.S. patent and published European patent applications. Primary alkanols are particularly preferred, largely on the basis of rate of the alkoxylation reaction. For reasons relating to the utility of the product alkoxylates in detergent formulations, preference may be expressed for alkanols within further restricted carbon number ranges. Thus, alkanols in the $C_9$ to $C_{16}$ range are preferred reactants, while those in the $C_9$ to $C_{15}$ range are considered more preferred and those in the $C_{11}$ to $C_{14}$ range most preferred. Still further preference for reason of product utility may be stated for alkanol reactants in which greater than about 50 percent, more preferably greater than about 70 percent, and most preferably greater than abut 90 percent of the alkanol molecules are of linear (straight-chain) carbon structure. Mixtures containing a variety of such alkanols, differing, for instance, with respect to carbon number and branching in the carbon chain, are suitable for purposes of the process of the invention and are in most cases preferred because of commercial availability.

The alkylene oxide (epoxide) reactant utilized in the process of the invention comprises one or more alkylene oxides, preferably the vicinal alkylene oxides having from 2 to 4 carbon atoms, including ethylene oxide, propylene oxide, and the 1,2- and 2,3-butylene oxides. Particularly preferred are ethylene oxide and propylene oxide, while the use of ethylene oxide is most preferred. Mixtures of alkylene oxides are suitable, in which case the product of the invention will be a mixed alkoxide.

The alkoxylation reaction of the process of the invention is necessarily carried out under alkaline pH and in the presence of one or more soluble compounds of calcium. The invention is generally of greatest advantage when the alkoxylation reaction is catalyzed by a soluble basic compound of calcium, although, if desired, the reaction can be principally catalyzed by another basic alkoxylation catalyst with the calcium present serving another function. If the alkoxylation is principally catalyzed by a calcium compound, addition may be made to the alkoxylation reaction mixture of either a calcium compound which is soluble and basic per se or a precursor which is converted to a soluble basic form of calcium upon interaction with the alkoxylation process reactants and/or the specified reaction activator. The calcium compound is described as soluble in the sense that it is soluble in a mixture of liquid alkanol reactant and alkoxylate product to the extent necessary to promote the desired reaction. At least about 0.05 percent by mole (%m) of the calcium compound, calculated on moles of total alkanol reactant, is typically necessary for the desired catalytic effect. Preferably, the calcium compound is present in the reaction mixture in a quantity between about 0.1 and 10%m calculated on alkanol, while a quantity between about 0.5 and 6%m is more preferred and between about 1 and 4%m is considered most preferred. As a rule, the rate of the alkoxylation reaction increases as the invention is carried out with increasing quantities of catalyst. The catalyst is described as basic in the conventional sense, indicating that a hydrolyzed sample of an alkoxylation reaction mixture containing the catalyst in a catalytically-effective quantity (e.g., a 10%w solution of the reaction mixture in water) has a pH greater than 7.0. For purposes of the invention, the overall reaction mixture is the basic pH. Examples of specific soluble, basic calcium compounds suitable for introduction into the reaction mixture as catalysts include the reaction products of calcium with various alcohols (for instance, alcoholates such as calcium alkoxides and phenoxides), as well as ammoniate, amide, thiolate, thiophanoxide and nitride compounds. Preferred for use as catalyst (or catalyst precursor) are the alcoholates, while the alkoxides in particular are considered more preferred. Each alkoxy group of such alkoxides has a carbon number that is preferably in the range from 1 to about 30, more preferably in the range from 1 to about 6. The most preferred calcium alkoxides are those having $C_1$, $C_2$ or $C_3$ alkyl groups, i.e., calcium methoxide, ethoxide and propoxide. Representative of suitable calcium catalyst precursors which are not per se soluble and/or basic but which are converted into soluble, basic compounds in the alkoxylation reaction mixture are the thiocyanates and the carboxylates, such as the formate, acetate, oxalate, citrate, benzoate, laurate, and stearate. Without intention that the invention be limited to one theory or mechanism of operation, it is speculated that soluble, basic calcium compounds which are added to or formed in the reaction mixture function to aid in the formation (by transalcoholysis reaction, or otherwise) of alkoxides of the alkanol reactant and/or of the alkoxylate product, which then more directly promote the desired alkoxylation.

The alkoxylation reaction promoted by a soluble basic compound of calcium is of particular advantage in view of its selectivity for a product having a narrow range of alkylene oxide adducts, that is, for a mixture of alkoxylate molecules in which a relatively large proportion have a number (n) of alkylene oxide adducts within a relatively narrow range of values. It is known that alkoxylate products having such a narrow-range distribution are preferred for use in detergent formulations. (Great Britain Pat. No. 1,462,134; Derwent Publications Research Disclosure No. 194,010.) Narrow-range alkoxylates are also known to be particularly valuable as chemical intermediates in the synthesis of certain carboxylated alkyl polyethers (U.S. Pat. No. 4,098,818) and of certain alkyl ether sulfates (Great Britain Pat. No. 1,553,561).

The relative selectivity of an alkoxylation process for a narrow-range product can be quantitatively expressed in terms of an index value (Q), calculated according to the equation $Q = \bar{n}P^2$ herein $\bar{n}$ is a mean average adduct number, determined as the ratio of the total moles of alkylene oxide reacted to form alkoxylate, to the total moles of alkanol either unreacted or reacted to form alkoxylate, and wherein P represents the highest selectivity of the reaction (in percent by weight) for alkoxylate product having any single common adduct number. (For instance, if the reaction product contained 10 percent by weight of alkoxylate molecules characterized by an adduct number of 5 and lesser quantities of molecules having any other single adduct number, then P for the reaction product would equal 10.) Higher values of Q indicate a more selective process and a more narrow-range product. For the typical ethoxylate products of greatest commercial interest, conventional alkoxylation of alkanols promoted by basic alkali metal (e.g. sodium or potassium) containing catalysts yields alkoxylates characterized by a value for Q of approximately 500, while a reaction promoted by a soluble, basic compound of calcium yield products characterized by a value for Q of approximately 1000 to 1200. Alkoxylation processes employing basic barium and strontium compounds as recently reported in the art (U.S. Pat. Nos. 4,210,764, 4,223,164 and 4,239,917 and the published European patent application Nos. 0026544, 0026546, and 0026547) also yield products having values of Q in the range from about 1000 to 1200.

Alkoxylation of alkanols in the presence of calcium catalysts also has advantage over reactions utilizing alkali metal catalysts with respect to the preparation of alkoxylates containing low levels of unreacted alkanol.

In terms of processing procedures, the alkoxylation reaction is preferably carried out by mixing the catalyst with the liquid alkanol reactant and then contacting the resulting solution with gaseous ethylene oxide at the specified temperature and pressure. The solution is then brought to the desired temperature and, by addition of alkylene oxide, preferably together with an inert gas, to the desired pressure. Alkoxylation typically commences after an induction period of a few minutes to a few hours. As the alkylene oxide is taken up in the reaction additional alkylene oxide is added, conveniently at a rate which maintains an approximately constant reaction pressure. Addition of alkylene oxide and its reaction of alkoxylate is continued until the product reaches the average alkylene oxide adduct number desired for the particular process. Generally, although not necessarily, the invention is best utilized in the preparation of alkoxylates having an average adduct number in the range of between about 1 and 15, expressed in terms of the total moles of alkylene oxide reacted per mole of alkanol. For reasons relating to utility of the alkoxylate in the broadest commercial applications the process is continued to yield a product having an adduct number that is preferably between about 2 and 12, more preferably between about 3 and 10, most preferably between about 4 and 9. The time required to complete a process in accordance with the invention, when using as catalyst one or more soluble, basic calcium compounds, is dependent both upon the degree of alkoxylation that is desired (i.e., upon the average adduct number of the product) as well as upon the rate of the alkoxylation reaction. This reaction rate is, in turn, dependent upon such parameters as reaction temperature, pressure, and catalyst concentration in the reaction mixture. Under most preferred operating conditions, preparation of an alkoxylate having an average alkylene oxide adduct number of about 3 can typically be accomplished in about 1 to 1.5 hour, while preparation of a product having an average adduct number of about 10 would require about 2.5 to 4.5 hours. These reaction times are merely illustrative and can be substantially reduced by operation at the higher reaction temperatures and/or pressures, although often at the expense of a selectivity loss in the utilization of the reactants to the desired alkoxylate products.

Following the alkoxylation reaction between the alkanol and alkylene oxide reactants under conditions of alkaline pH and in the presence of the soluble calcium compound, the alkoxylate product mixture is neutralized by addition of an acid. As used herein, neutralization means decreasing the pH of the basic reaction mixture to a value which is about equal to or less than 7. For purposes of the present invention, this acid is necessarily one or more compounds selected from the group consisting of propionic acid and benzoic acid. Use of one or both of the indicated acids for neutralization of the basic, calcium-containing reaction mixture has been found to be critical to the preparation of a product having desirable properties. For instance, neutralization of the reaction mixture with these acids yields a product having essentially the same low viscosity, high clarity, and low color as are characteristic of the unneutralized mixture. However, when other carboxylic acids, for example, formic, acetic, butyric, hexanoic, oxalic, tartaric and citric acids, are added to the same reaction mixture for neutralization purposes, the mixture thickens to a gel-like consistency and/or forms a precipitate. Moreover, such gel formation in the alkoxylate appears unique to the presence of calcium ions. Alkali metal, e.g., sodium and potassium, and other alkaline earth metals, e.g., barium and strontium, when present in alkoxylation mixtures do not give rise to similar gelation problems.

Apart from use of the specified acids, procedures suitable for the neutralization step of the invention are not found to be critical. In general, procedures as have been employed in the prior art to accomplish neutralization of basic alkoxylation reaction mixtures can also be employed in carrying out the invention. Preferably, the acid is mixed directly with the basic reaction mixture, after the mixture has first been cooled to a temperature below that at which the alkoxylation was conducted, for instance, a temperature in the range of about 20° to 100° C. As in conventional practice, the quantity of acid is that sufficient to effectively inactivate the basic alkoxylation catalyst. Typically, addition of acid is made to decrease the pH of the mixture to a value less than or equal to about 7.0. Neutralization to a pH in the range from about 5 to 7 is preferred, while a pH in the range from about 5.5 to 6.5 is considered most preferred.

The present invention is most effective when essentially only the propionic and/or benzoic acids are added to the alkoxylation reaction mixture for neutralization purposes. However, the gel and precipitate inhibiting properties of these acids are also at least partially effective when employed in mixtures with other acids, e.g., a mixture containing equal quantities by weight of propionic acid and acetic acid. Accordingly, neutralization using such mixtures of the specified acid, that is, propionic and/or benzoic acid, with other acids is intended to come within the scope of the invention.

In terms of distinctions in the quality of the neutralized alkoxylation product, the process of the invention is applied to best advantage when the specified acid is added to an alkoxylation mixture containing more than about 200 ppmw (parts per million by weight) calcium, particularly between about 500 and 10,000 ppmw calcium, and most particularly between about 1,000 and 5,000 ppmw calcium.

The invention is further illustrated by reference to the following examples and comparative examples.

EXAMPLE 1

A process according to the invention was conducted under the following procedures:

An alkoxylation reaction was carried out in a 300 ml stainless steel autoclave reactor. The alkanol reactant was a NEODOL ®23 Alcohol (trademark of and sold by Shell Chemical Company), characterized as a mixture of primary, 80% linear (20% branched) alkanols containing twelve and thirteen carbon atoms (about 40% by mole $C_{12}$, 60% by mole $C_{13}$). Initially, the liquid alkanol reactant was dried to a water content about 40 ppm (as indicated by Karl Fischer water analysis) by sparging nitrogen at 130° C. for 35 minutes. To about 65 grams (335 millimoles) of the dried alkanol was added about 1.6 grams (10 millimoles) of calcium ethoxide as alkoxylation catalyst. The resulting catalyst solution in the alkanol reactant was sparged with nitrogen at 130° C. for 30 minutes. The solution was then transferred to the reactor under a nitrogen atmosphere, the system sealed, heated to 170° C. and pressurized with nitrogen and alkylene oxide reactant, in this case ethylene oxide, to a total pressure of about 70 psig (55 psia nitrogen and 30 psia ethylene oxide). Alkoxylation (ethoxylation) commenced immediately and the temperature was maintained at 170° C. Ethylene oxide was added to the reactor system upon demand that is, to maintain approximately constant reaction pressure. About 96 grams (2.17 moles) of ethylene oxide was added over a three hour period. The reactor was then maintained at 170° C. for an additional 30 minutes without addition of further ethylene oxide, to consume unreacted ethylene oxide in the system.

Following the alkoxylation step, 100 grams of the reaction product mixture was cooled to about 70° C. and transferred under nitrogen to a sample bottle. This mixture contained in solution about 2500 parts per million by weight (ppmw) of calcium ion. Titration of the product mixture with aqueous hydrochloric acid indicated a content of 0.017 milliequivalent of calcium ion per gram of alkoxylate. Neutralization was accomplished by mixing the 100 grams of alkoxylation product mixture with 10.7 milliequivalents of propionic acid. The neutralized mixture was maintained at 70° C. for thirty minutes and then cooled to about 25° C. Hydrolysis of an aliquot of the neutralized mixture at 25° C. indicated a pH of about 7.0.

The product of this process was a clear, nearly colorless solution characterized by low viscosity and an absence of precipitate formation.

EXAMPLE 2

The procedures of Example 1 were again followed, in this case, however, utilizing benzoic acid in the place of propionic acid in the neutralization step. Again the product was a clear, essentially colorless solution, without noticeable precipitate, having acceptably low viscosity.

COMPARATIVE EXAMPLES

The procedures were again followed with substitution in the neutralization step of a number of other carboxylic acids the use of which is not in accordance with the invention. The use of acetic acid resulted in an apparently homogeneous semi-solid or gelatinous product. Butyric acid and hexanoic acid were responsible for production of a two phase mixture containing roughly equal quantities of a lower gel phase and an upper liquid phase. Formic acid, oxalic acid, and carbonic acid each resulted in formation of a white precipitate.

EXAMPLE 3

A series of experiments was carried out to quantify aspects of the invention relating to viscosity of neutralized calcium-containing alkoxylate products. Alkoxylation reaction mixtures containing catalytic quantities of calcium in solution and having alkaline pH were simulated by addition of various levels of calcium ethoxide to a previously-prepared ethoxylate product. This ethoxylate product had been prepared by reaction between the NEODOL ®23 Alcohol and an average of 6.5 moles of ethylene oxide per mole of alkanol, in the presence of a potassium hydroxide catalyst, followed by neutralization with acetic acid. Although the calcium-containing ethoxylate mixtures thus obtained also contained a residue of both potassium (about 1040 ppmw) and acetate ions, this was determined not to have significant influence upon the desired comparisons.

After addition of the calcium ethoxide to the ethoxylate, the resulting mixtures were sparged with nitrogen at 130° C. for one hour to remove ethanol formed by transalcoholysis reaction. The liquid mixtures were then cooled to 50° C. and neutralized by addition with mixing of either propionic acid (according to the invention) or acetic acid (not according to the invention). Acid was added until the pH of a hydrolyzed aliquot decreased to 7.0 (±0.2).

The absolute viscosity, in centipoise (cp), of each resulting neutralized, calcium-containing alkoxylate mixture was determined at one or more temperatures. Results are presented in the following Table I and also in the attached drawing.

TABLE I

| experiment number | calcium ion concentration (ppmw) | acid used in neutralization | temperature of viscosity measurement (°C.) | absolute viscosity (cp) |
|---|---|---|---|---|
| 0 | 0 | acetic | 25 | 110 |
|   |   |        | 38 | 31 |
| 1 | 250 | acetic | 38 | 195 |
| 2 | 500 | acetic | 38 | 225 |
| 3 | 750 | acetic | 38 | 420 |
| 4 | 1250 | acetic | 38 | 475 |
| 5 | 2500 | acetic | 25 | 4500 |
|   |      |        | 38 | 590 |
| 6 | 750 | propionic | 25 | 126 |
| 7 | 1250 | propionic | 38 | 60 |
| 8 | 2500 | propionic | 25 | 310 |
|   |      |           | 38 | 81 |

The influence of both the calcium ion concentration and the acid utilized for neutralization on the viscosity of the resulting ethoxylate mixture are readily apparent from the comparisons presented in the Table and the drawing. Particularly notable are the benefits provided by neutralization with propionic acid of ethoxylation mixtures having a concentration of calcium ion in excess of about 1000 ppmw, as would typically result from the use of a calcium compound as an alkoxylation catalyst. At such levels of calcium, the viscosities of the propionic acid neutralized ethoxylates are roughly an order of magnitude less than those neutralized with acetic acid.

EXAMPLE 4

This example illustrates that the presence of calcium ion and the nature of the acid used for neutralization have a like effect upon the viscosity of different alkoxylate mixtures. Several different alkoxylate products were prepared by reacting substantially primary and linear alkanols of several carbon number ranges with amounts of ethylene oxide, in different average molar ratios of ethylene oxide to alkanol (i.e., n in formula III herein). As in Example 3, these reactions were conducted using potassium hydroxide as catalyst and acetic acid to neutralize the reaction mixture. Calcium ethoxide was added to each of the different ethoxylates to simulate a calcium-containing alkoxylation mixture of alkaline pH. Each mixture contained 2500 ppmw of calcium ion. Following addition of the calcium ethoxide, the mixtures were sparged with nitrogen at 130° C. for one hour, and cooled to 50° C. Each mixture was divided into equal portions; one of which was neutralized with acetic acid while the other was neutralized with propionic acid in accordance with the invention. Sufficient acid was added so that the pH of a hydrolyzed aliquot of the neutralized mixture had a pH of 7.0 ($\pm 0.2$). Viscosities were determined at 38° C. Results are summarized in Table II.

TABLE II

| ethoxylate preparation | | calcium ion concentration (ppmw) | acid | viscosity at 38° C. (cp) |
|---|---|---|---|---|
| alkanol carbon no. | average value of n | | | |
| 12 to 15 | 3 | 2500 | propionic | 17 |
|          |   |      | acetic | 3500 |
| 12 to 15 | 9 | 2500 | propionic | 440 |
|          |   |      | acetic | 2440 |
| 12 to 15 | 12 | 2500 | propionic | 375 |
|          |    |      | acetic | 1162 |
| 9 to 11 | 6 | 2500 | propionic | 177 |
|         |   |      | acetic | 1120 |
| 14 and 15 | 7 | 2500 | propionic | 242 |
|           |   |      | acetic | 770 |
| 14 and 15 | 13 | 2500 | propionic | 550 |
|           |    |      | acetic | 6800 |
| 12 and 13 | 3 | 2500 | propionic | 180 |
|           |   |      | acetic | 1600 |

I claim:

1. A process for the preparation of alkanol alkoxylates which comprises steps for alkoxylating one or more alkanols having carbon number in the range from 8 to 18 by reaction with one or more alkylene oxides having carbon number in the range from 2 to 4 under alkaline pH and in the presence of one or more soluble compounds of calcium, and neutralizing the resulting alkoxylation mixture by addition thereto of an acid selected from the group consisting of propionic acid, benzoic acid, and mixtures thereof.

2. The process of claim 1, wherein the acid is propionic acid.

3. The process of claim 1 or claim 2, wherein the alkanols are of a carbon number in the range from 9 to 15 and the alkylene oxides are of a carbon number of 2 or 3.

4. The process of claim 3, wherein the alkylene oxide is ethylene oxide.

5. The process of claim 4, wherein the alkoxylation reaction is catalyzed by a soluble, basic compound of calcium.

* * * * *